US008828424B2

(12) United States Patent
Bray

(10) Patent No.: US 8,828,424 B2
(45) Date of Patent: *Sep. 9, 2014

(54) ANTIBACTERIAL WOUND DRESSING

(75) Inventor: Roger Bray, Nuneaton (GB)

(73) Assignee: Convatec Limited (GB)

( * ) Notice: Subject to any disclaimer, the term of this patent is extended or adjusted under 35 U.S.C. 154(b) by 1303 days.

This patent is subject to a terminal disclaimer.

(21) Appl. No.: 10/488,305

(22) PCT Filed: Sep. 11, 2002

(86) PCT No.: PCT/GB02/04131
§ 371 (c)(1),
(2), (4) Date: Mar. 1, 2004

(87) PCT Pub. No.: WO03/022317
PCT Pub. Date: Mar. 20, 2003

(65) Prior Publication Data
US 2004/0241213 A1  Dec. 2, 2004

(30) Foreign Application Priority Data

Sep. 12, 2001 (GB) .................................. 0121946.8
Nov. 27, 2001 (GB) .................................. 0128329.0

(51) Int. Cl.
*A61L 15/00* (2006.01)
*A61L 15/46* (2006.01)
*A61L 15/28* (2006.01)

(52) U.S. Cl.
CPC ........... *A61L 15/46* (2013.01); *A61L 2300/104* (2013.01); *A61L 2300/404* (2013.01); *A61L 15/28* (2013.01)
USPC ....................................................... 424/445

(58) Field of Classification Search
USPC ........................................... 424/443, 445, 449
See application file for complete search history.

(56) References Cited

U.S. PATENT DOCUMENTS

| | | | | |
|---|---|---|---|---|
| 4,643,918 | A | 2/1987 | Orban | 427/304 |
| 4,752,536 | A | 6/1988 | Shimizu et al. | 428/607 |
| 5,186,984 | A | 2/1993 | Gabbert | 427/443.1 |
| 5,302,415 | A | 4/1994 | Gabara et al. | 427/306 |
| 5,709,870 | A * | 1/1998 | Yoshimura et al. | 424/404 |
| 5,731,083 | A | 3/1998 | Bahia et al. | 428/393 |
| 6,075,177 | A | 6/2000 | Bahia et al. | 602/43 |
| 6,153,214 | A * | 11/2000 | Horsler | 424/443 |
| 6,471,982 | B1 * | 10/2002 | Lydon et al. | 424/443 |
| 6,548,730 | B1 * | 4/2003 | Patel et al. | 602/56 |
| 6,835,678 | B2 * | 12/2004 | Jackson et al. | 442/154 |
| 6,897,349 | B2 * | 5/2005 | Gibbins et al. | 602/48 |
| 2003/0180346 | A1 | 9/2003 | Woods | 424/446 |

FOREIGN PATENT DOCUMENTS

| | | | | |
|---|---|---|---|---|
| DE | 2639287 | | 9/1978 | |
| EP | 0361722 A2 | | 4/1990 | |
| EP | 0673451 | * | 10/1996 | |
| GB | 927115 | | 5/1963 | |
| GB | 1328088 | | 8/1973 | |
| WO | WO 91/11206 A1 | | 8/1991 | |
| WO | WO 92/16589 A1 | | 10/1992 | |
| WO | WO 92/22285 A1 | | 12/1992 | |
| WO | WO 9222285 | * | 12/1992 | ............... A61K 9/70 |
| WO | WO 93/12275 | | 6/1993 | |
| WO | WO94/16746 | * | 8/1994 | |
| WO | WO 94/16746 A1 | | 8/1994 | |
| WO | WO 9416746 | * | 8/1994 | ............... A61L 25/00 |
| WO | WO 01/24839 A1 | | 4/2001 | |
| WO | WO 0124839 | * | 4/2001 | ............... A61L 15/22 |
| WO | WO 02/24240 A1 | | 3/2002 | |
| WO | WO 02/36866 A1 | | 5/2002 | |
| WO | WO 02/43743 A1 | | 6/2002 | |

OTHER PUBLICATIONS

Odian, George. Principles of Polymerization, 3rd Edition, 1991, John Wiley & Sons, Inc. p. 713.*
Derwent, One page English abstract of DE 2639287, Sep. 1978.
Derwent, two page English abstract of JP 1207473 A, Aug. 1989.
Derwent, two page English abstract of JP 2153076 A, Jun. 1990.
Derwent, one page English abstract of JP 4146218 A, May 1992.

* cited by examiner

*Primary Examiner* — Snigdha Maewall

(57) ABSTRACT

An antibacterial wound dressing is based on, or derived from, gel-forming fibres such as carboxymethyl cellulose or alginate fibres having silver ions linked thereto at some but not all of the exchangeable sites such that the distribution of silver ions over the exchangeable sites is substantially uniform. The silvered fibres for the wound dressing can be prepared by contacting an assembly of precursor gel-forming fibres having exchangeable sites under conditions which do not cause irreversible gelling of the fibres with an amount of a solution containing silver ions so as to link silver ions at some but not all of the exchangeable sites, the whole of the assembly of precursor gel-forming fibres being contacted essentially simultaneously with the entire solution containing silver ions.

16 Claims, No Drawings

ANTIBACTERIAL WOUND DRESSING

FIELD OF THE INVENTION

The present invention relates to wound dressings, in particular to an antibacterial wound dressing based on silvered gel-forming fibres, and to an improved process for the manufacture of such a wound dressing.

BACKGROUND OF THE INVENTION

It has been known for many years that silver is a useful antibacterial agent with broad-spectrum activity together with compatibility with mammalian tissue, and there have been many proposals to incorporate silver into wound dressings to obtain the advantage of the bactericidal properties of silver in a wound dressing. In addition, silver has been applied to fibrous material previously for non-wound dressing purposes, usually for the purpose of enhancing electrical conductivity, see for example UK-A-927,115, WO-A-92/16589, DE-C-2,639,287, U.S. Pat. Nos. 5,302,415, 5,186,984, 4,752,536, 4,643,918, JP-010207473A, and JP-020153076. Silver has been applied to such fibres, which are generally not gel-forming, in a variety of ways in those references, some of which involve immersing the fibres into a silver solution, but detail of the procedures used is often lacking.

Carboxymethyl cellulose, in particular carboxymethylated lyocell, has the ability to absorb a great deal of water and to form a gel on its surface. This property of the material has been found to be particularly advantageous in the formation of wound dressings that are both absorbent and gel-forming. The carboxymethylation of cellulose is described in WO-A-93/12275, and the use of carboxymethyl cellulose for wound dressings is described in WO-A-94/16746. Calcium (or sodium/calcium) alginate is another material useful in the formation of wound dressings, because of its absorbency and gelling capability. Gel-forming fibres for use in wound dressings are water-absorbent fibres which become moist and slippery or gelatinous upon the uptake of wound exudate and thus reduce the tendency for the surrounding fibres to adhere to the wound. The gel-forming fibres may also swell. Gel-forming fibres can be of the type which retain their structural integrity on absorption of exudate or can be of the type which lose their fibrous form and become a structureless gel or solution on absorption of exudate. GB-A-1,328,088, WO-A-91/11206, WO-A-92/22285, JP-A-4146218 and WO-A-02/36866 disclose the incorporation of silver into calcium sodium alginate, WO-A-01/24839 discloses carboxymethyl cellulose fibres containing silver chloride and WO-A-02/43743 discloses incorporating silver into a polymer which can be carboxymethyl cellulose or an alginate, the contents of these documents being incorporated by reference herein.

There have, however, been particular problems associated with the use of silver in wound dressings because of the fact that silver compounds are light-sensitive and darken on exposure to light. This can result in the production of products which have an unattractive visual aspect, even if they are technically suitable for use as wound dressings.

There are three particular aspects of the darkening of the silver compound in light which need to be addressed when seeking to produce a commercially acceptable silvered wound dressing. One aspect is the actual colour of the product, namely the need to have a product having a colour acceptable to the consumer. The second aspect is the need to produce a product having a uniform appearance. The third aspect is the stability (shelf-life) of the colour of the dressing within whatever packaging is used to package the dressing. If fibres are blended, and both fibres are white, any imperfection in the blending is not noticed by the consumer. Whilst this is primarily a visual issue, extremes of streakiness or discoloration within a wound dressing could be an indicator of incomplete or inadequate silver additions to the wound dressing or parts of it, or even the presence of excessive amounts of silver in some areas, which could indicate potential problems in use. Silver as an antibacterial material should be used in measured dosages, and this would not be the case if the silver level varied from dressing to dressing.

Kiers are well known for use in fibre treatment processes; for example, it is well known that cellulosic fibre can be dyed by being placed into a kier and the dye liquor pumped through the kier to give a product having a uniformly dyed appearance. A kier is a sealed container having inlets and outlets; it is capable of being pressurised and heated if required and is incorporated into a circuit such that liquor can be pumped through the kier. Located within the kier is a porous basket in the form of a stainless steel mesh and the product to be treated is packed consistently in the mesh to ensure uniform and even flow of liquor through the mesh during the pumping process.

Attempts were made, therefore, by the applicant to apply the silver to carboxymethyl cellulose fibre in a kier just as though the carboxymethyl cellulose was being dyed with a dye, using a solution of a silver-containing compound (industrial methylated spirit (IMS), $H_2O+AgNO_3$) in the kier. The silver-containing liquor was pumped from the centre towards the periphery. In that procedure a basket containing 1.25 kg of the carboxymethyl cellulose fibre was placed within the kier prior to charging the kier with liquor. Then 10.4 litres of a solution of (IMS, $H_2O+AgNO_3$) made up of 6.41 IMS, 4.01 water, 25 g $AgNO_3$ at a silver concentration of 0.240 w/v and a temperature of 30° C. were pumped through the kier, which had a capacity of about 12 litres. After the liquor had been pumped around the circuit for 30 minutes, the liquor was drained out of the fibre and the product was moved immediately to subsequent stages, including the application of a textile finish and drying. After all of the subsequent treatments had taken place the fibre was removed and exposed to light. It was found that the fibre was not uniform in its silver take-up. The product produced by this process was found to be very streaky.

Attempts were therefore made to alter the kier process by using an upward-flow basket which fed the liquor from below rather than from the centre. Such a procedure was found to improve the product in the sense that it was less streaky but there was a distinct gradation of silver take-up from the bottom to the top of the basket.

It is an object of the present invention to provide an antibacterial wound dressing based on or derived from silvered gel-forming fibres in which the above disadvantages are reduced or substantially obviated. It is a further object of the present invention to provide silvered fibres for an antibacterial wound dressing based on silvered gel-forming fibres in which the above disadvantages are reduced or substantially obviated.

DISCLOSURE OF THE INVENTION

We have found that superior wound dressings can be obtained from silvered gel-forming fibres having more sites capable of taking up silver ions than there are silver ions available in the solution used for silvering, so that not all the sites take up silver ions in the silvering operation, by having the silver ions that are taken up distributed substantially uniformly over the sites capable of taking them up.

Antibacterial wound dressings according to the invention are thus derived from gel-forming fibres having silver ions linked thereto at some but not all exchangeable sites and are characterized in that the distribution of silver ions over the exchangeable sites is substantially uniform.

Usually, only a minority of the sites on the gel-forming fibres capable of ionic exchange with silver ions are actually silvered in making the wound dressings of the invention, and frequently not more than 20%, often not more than 10%, of such sites are silvered.

We have also found that superior silvered fibres for wound dressings can be obtained if the contacting of the gel-forming fibres having exchangeable sites capable of exchange with silver ions to silver the fibres with the solution for silvering is carried out in such a way that the entire solution for silvering is contacted essentially simultaneously with the entire amount of gel-forming fibres to form the wound dressing, rather than being contacted gradually or partially.

According to the invention, therefore, a process for producing silvered fibres for antibacterial wound dressings based on silvered gel-forming fibres includes the steps of:

(i) forming an assembly of precursor gel-forming fibres having thereon exchangeable sites capable of exchange with silver ions to link silver ions to the fibres, and (ii) contacting the assembly of precursor gel-forming fibres with a solution containing silver ions, under conditions which do not cause irreversible gelling of the fibres, thereby to link silver ions to the fibres at exchangeable sites, and it is characterised in that the whole of the assembly of precursor gel-forming fibres to form the wound dressing is contacted essentially simultaneously with the entire solution containing silver ions, the solution containing silver ions being used in an amount such that only enough silver ions are present to link with some but not all of the exchangeable sites on the precursor gel-forming fibres.

The essentially simultaneous contacting may be achieved as a batch process by rapidly dipping and immersing in the silver-containing solution the gel-forming fibres to form the wound dressing.

Thus, in one embodiment, the present invention provides a process for the production of an antibacterial wound dressing based on silvered gel-forming fibres, which process includes the following steps in sequence:

(i) forming precursor fibres having thereon sites capable of ionic exchange with silver ions to form a silvered tow, and (ii) silvering the fibres using a silver-containing solution which does not cause irreversible gelling of the fibres, characterised in that, in order to give a uniform take-up of silver, the fibres are dunked into the silver solution, by lowering the fibres directly into the solution and pushing the fibres immediately below the surface of the solution. The resulting silvered fibres may then be processed, for example in conventional steps, to form the wound dressing.

Gel-forming fibres suitable for use in wound dressings tend to be extremely reactive towards silver ions, that is to say the silver ions bind very quickly and very firmly to the ion-exchange sites on the fibres. We have found that, in contrast to dye molecules applied in a kier, there is essentially no redistribution of silver ions after initial attachment. This means that, if such fibres are brought slowly or gradually into contact with a solution containing a limited amount of silver ions, the portions of the fibres first in contact with silver-containing solution will take up relatively large quantities of silver ions so that those portions of the fibres coming into contact with the silver-containing solution last may have hardly any take-up of silver at all. The resulting fibres will not have a uniform coloration initially and will darken to different degrees. It would not be possible to overcome this drawback by using a larger quantity of silver, because that could lead to over-silvering of the parts of the fibres first in contact with the solution, with consequent lack of uniformity of silver distribution in the product, or to the failure to exhaust the silver content of the solution, with consequent problems over disposal of effluent as well as waste of valuable silver.

It is also important that the volume of the solution is adjusted so that essentially all parts of it contact gel-forming fibres essentially simultaneously. If the volume of the solution is large compared to the volume that is taken up by the gel-forming fibres, so that some parts of the solution are relatively remote from any fibres, silver ions in that part will tend to diffuse towards and interact with the fibres first encountered and give heavier deposition on those fibres, spoiling the uniform distribution desired.

It is particularly preferred for the volume of the solution with which the precursor gel-forming fibres are contacted to be adjusted such that essentially all the liquid of the solution is taken up by the water-absorbent gel-forming fibre, leaving essentially no free liquid. In such a situation there is essentially no waste solution to be disposed of at this stage.

The time interval between the beginning of the dipping of the gel-forming fibre into the silver-containing solution and the moment at which sufficient gel-forming fibre to form the wound dressing is entirely immersed is desirably not more than about 10 seconds, preferably 5 seconds or less. For practical purposes the time interval is usually about 2 to 3 seconds.

It has surprisingly been found that by dunking the fibre in an unconstrained manner into the solution, a very uniform silver take-up occurs. Furthermore, it has been found that it is desirable to minimise the amount of silver-containing solution to produce a silvered gel-forming fibre. The minimum volume of liquid required completely to cover any given amount of gel-forming fibre when the fibre is dunked into the solution can readily be determined by experiment. Once the minimum volume of liquid has been determined then that amount of silver-containing solution is made up and the fibre is simply dunked into the solution so that the fibre takes up the solution, that is to say it fills the solution within the container in which it is held. This means that there is minimal wasted solution and the amount of silver-containing solution which has to be handled is also minimised.

The silver-containing solution is preferably held in a container, which may be a closed container or an open container. The size of the container, and hence the volume of solution it contains, and the amount of gel-forming fibre are correlated so that the entire volume of solution contacts fibres essentially simultaneously.

The gel-forming fibre is preferably a carboxymethylated cellulose (CMC) fibre. The CMC derived from lyocell generally has a degree of substitution of from 0.1 to 0.5, preferably 0.2 to 0.4. This gives a sufficient number of carboxylate groups that the gelling and absorbency properties are adequate for use as a wound dressing but without being so high that a substantial amount of the fibre becomes soluble. The CMC may be derived from cellulose, preferably from lyocell, by carboxymethylation. An alternative fibre is calcium or sodium/calcium alginate. The fibre which is contacted with the silver-forming solution is preferably dry, although it may be pre-wetted with a liquid which does not cause irreversible gelling. It is preferably in the form of a hank or tow but can alternatively be in staple (cut) fibre form, eg in standard, conventional lengths. To facilitate rapid fibre/solution contact the fibre is preferably used in relatively open, unconstrained form as opposed to tightly packed, constrained form. A hank of fibre, essentially a fairly loose bundle of continuous tow, or cut fibres achieves this. It is preferred in commercial operation to contact the solution essentially simultaneously with enough fibre to form more than one wound dressing, for example from 1,000 to 10,000 dressings. Thus, hanks up to many metres, for example 20 to 200 metres or more, long may be used. The fibre may have a soft finish thereon.

The silver content of the silvered fibres is generally of the order of 0.01 to 10%, more narrowly 0.1 to 5%, preferably 0.5 to 2%, more preferably 0.9 to 1.5%, by weight. This enables good antibacterial activity to be achieved, without toxicity problems arising. This compares with a theoretical maximum of the order of 16% if all exchangeable sites on CMC lyocell with a degree of substitution of 0.3 are exchanged and about 38% if all exchangeable sites on conventional alginate fibre are exchanged.

The contacting is carried out such that irreversible gelling of the fibres is avoided. It is preferred to use an aqueous organic solution for the silver ions, especially an aqueous alcoholic solution such as a mixture of ethyl alcohol and water. The water content of such a solution will generally not exceed about 50% by volume and is preferably 25 to 50% by volume. The silver is provided in the form of a source of soluble silver ions, for example a soluble silver salt of an acid, such as silver nitrate. Solubility at the required concentration in the solution to be used is essential, so that substances such as ceramic, ion-exchange resins containing silver or other insoluble silver sources should not be used. Broadly speaking, the silver content of the bath may be of the order of 0.1 to 1% w/v, preferably 0.25 to 0.5% w/v. A typical solution may for example comprise 2.71 IMS (industrial methylated spirit), 1.81 water and 25 g $AgNO_3$ to give a concentration of 0.35% w/v silver.

It may be desirable to stir or agitate the fibre or container during and/or immediately after addition so as to facilitate contact of all the fibre with all the solution.

If a continuous process, rather than a batch process, is required, the fibre could be fed down a pipe or tube in co-current with the desired rate of feed of silver solution so as to give the desired amount of silver content on the gel-forming fibre.

If no further wet processing steps are required prior to drying, the silvered fibres, suitably in the form of a tow, can then be squeezed out, preferably to approximately 1.5-21 remaining liquor per kg tow. This squeezing can be carried out manually or can be mechanised, for example by the application of vacuum pressure or via a press. Alternatively, the tow can be drained down and centrifuged. As the attachment of silver ions occurs very rapidly it is not necessary to remove the liquor from contact with the silvered fibres rapidly or essentially simultaneously in order to achieve a uniform silver deposition but in practice this may be preferred in case other unwanted effects occur.

Little silver normally remains in the squeezed-out liquor, since virtually all has reacted with the gel-forming fibre. This can be shown by testing the liquor with NaCl solution, whereupon hardly any precipitation is observed.

The resulting silvered tow of gel-forming fibre can then be processed into a wound dressing in known manner, for example as disclosed in WO-A-94/16746, the contents of which are incorporated herein by reference.

Additional wet processing steps can be carried out on the silvered fibre prior to drying. For example, a conventional textile finish may preferably be applied in conventional amount (e.g. about 0.5% w/v) from an aqueous organic liquor (e.g. IMS/water) which does not cause irreversible gelling of the fibre. This may be preceded by a treatment conferring photostability, for example a treatment such as disclosed in WO 02/43743 (incorporated herein by reference) involving a metal halide such as sodium chloride.

The dried silvered fibre, after cutting if necessary, typically into 50 mm staple lengths, may then be processed to form a nonwoven web, for example using a textile card and cross-folder. The web may then be treated to improve its strength, for example by needle bonding, before being cut into the dressing sizes required, for example squares typically of 10 cm×10 cm. The cut pieces may then be packaged, usually into individual pouches, and sterilized in a conventional manner, for example using gamma irradiation, before being ready for use.

The results of making this change are illustrated by the following Examples

EXAMPLE I

The kier process described above and the process according to the invention were carried out separately on carboxymethylated lyocell having a degree of substitution of about 0.3. The kier process was carried out as described under 'Background of the Invention'. The process according to the invention was carried out using a solution comprising 2.71 IMS, 1.81 water and 25 g $AgNO_3$ on a hank of carboxymethylated lyocell dipped and immersed entirely in the solution over a period of about 5 seconds so that the hank took up the solution and thus all parts of the solution were in contact with the carboxymethylated lyocell and essentially all taken up. The silvered hank obtained in that way had an average silver content essentially the same as the hank treated by the kier process. In each case, the reacted tow was spread out lengthwise and allowed to dry, not in the dark but exposed to light. The material made using the kier showed extremely different extents of grey or pink with the majority of the tow uncoloured, typically 75%. The material made by the process of the invention was mostly grey/pink coloured with perhaps as little as about 5% to 10% uncoloured tow.

The improvement was illustrated further when the tow was dried in the absence of daylight and cut/opened/carded/needled and examined as a piece of fabric. When these fabrics were exposed to intense daylight (eg 1000× standard) for 30 minutes the material made using the kier showed patchiness whereas the material made by the method of the invention was completely uniform in colour.

As a further experiment not according to the invention, the tow of fibre, rather than being lowered as a hank, in about five seconds in all, was fed into the container of silvernitrate-containing solution as an end feed, hand over hand. This meant that it took about fifteen seconds to lower the tow into the solution. After the fibre had been dried, the tow was exposed to light to show the silver take-up visually and laid out side-by-side on a white bench top with the tow according to the invention as produced above. The tow lowered hand-over hand in an end feed was deeply coloured over about the first ⅓ to ½ of its length and the end to go in last was very lightly coloured and patchy. The hank-lowered tow was substantially uniformly coloured along its length.

EXAMPLE II

Two solutions of silver nitrate (1.58 g) in water (1 litre) were made up in the laboratory at room temperature. To the first was added alginate tow (100 g) in a deliberately slow manner, i.e. it took approximately 30 seconds to achieve full immersion. To the second was added a similar amount of alginate tow but this time in less than 5 seconds.

Both tows were removed from the solution and, after squeezing out excess liquor, laid on the laboratory bench exposed to daylight. Soon afterwards but more so the following day, a vast difference was clearly visible. The slow-immersion tow was dark (due to discoloration caused by silver take-up) at one end of the tow but mostly uncoloured at the other end of the tow. The fast immersion tow was discoloured along the full length to a noticeably uniform extent.

In a production situation the water-based solution would be replaced with an IMS/water-based solution to avoid filament adherence and gelling caused by hydrogen bonding when water only is used.

The invention claimed is:

1. A process for producing silvered fibres for use in antibacterial wound dressings including the steps of
   (i) forming an assembly of precursor gel-forming fibres having thereon exchangeable sites capable of exchange with silver ions to link silver ions to the fibre,
   (ii) forming a solution containing silver ions comprising a soluble silver salt and an aqueous organic solvent, and
   (iii) essentially simultaneously contacting the assembly of precursor gel-forming fibres with the solution containing silver ions under conditions which do not cause irreversible gelling of the fibres, thereby to link silver ions at exchangeable sites, in which process the whole of the assembly of precursor gel-forming fibres is contacted essentially simultaneously with the entire solution containing silver ions, rather than being contacted gradually or partially, the solution containing silver ions being used in an amount such that enough silver ions are present to link with not more than about 20% of the exchangeable sites on the precursor gel-forming fibres, wherein the distribution of silver ions over the exchangeable sites is essentially uniform as shown by the essentially uniform coloration of the dressing.

2. A process according to claim 1, in which the process is a batch process wherein the assembly of precursor gel-forming fibres is contacted with the solution containing silver ions by dipping it rapidly and entirely into the solution.

3. A process according to claim 2, wherein the solution is held in a container and is an amount required completely to cover the precursor gel-forming fibres so that the fibres fill the solution within the container.

4. A process according to claim 2, wherein the time interval between the beginning of the dipping of the assembly of precursor gel-forming fibres to form the wound dressing into the solution and the moment at which the assembly of precursor gel-forming fibres to form the wound dressing is entirely dipped into the solution is not more than about 10 seconds.

5. A process according to claim 4, wherein said time interval is not more than 5 seconds.

6. A process according to claim 2, wherein the assembly of precursor gel-forming fibres to be dipped is dry.

7. A process according to claim 3, wherein the solution containing silver ions is held in a closed container.

8. A process according to claim 3, wherein the solution containing silver ions is held in an open container.

9. A process according to claim 1, wherein the precursor gel-forming fibres are in tow form or staple fibre form.

10. A process according to claim 1, wherein the assembly of precursor gel-forming fibres is in the form of a hank.

11. A process according to claim 1, wherein eh precursor gel-forming fibres are carboxymethyl cellulose fibres.

12. A process according to claim 11, wherein the carboxymethyl cellulose fibre is carboxymethylated lyocell.

13. A process according to claim 12, wherein the carboxymethylated lyocell has a degree of substitution of 0.2 to 0.4.

14. A process according to claim 1, wherein the precursor gel-forming fibres are calcium alginate or sodium-calcium alginate fibres.

15. A process according to claim 1, wherein the assembly of silvered, gel-forming fibres is processed to form wound dressings.

16. A process according to claim 1, wherein the solution containing silver ions is used in an amount such that enough silver ions are present to link with not more than about 10% of the exchangeable sites on the precursor gel-forming fibres.

* * * * *